United States Patent
Sur (10) Patent No.: US 10,231,485 B2
(45) Date of Patent: Mar. 19, 2019

(54) RADIO FREQUENCY TO DIRECT CURRENT CONVERTER FOR AN AEROSOL DELIVERY DEVICE

(71) Applicant: RAI Strategic Holdings, Inc., Winston-Salem, NC (US)

(72) Inventor: Rajesh Sur, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 389 days.

(21) Appl. No.: 15/205,903

(22) Filed: Jul. 8, 2016

(65) Prior Publication Data

US 2018/0007969 A1    Jan. 11, 2018

(51) Int. Cl.
| | |
|---|---|
| A61H 33/12 | (2006.01) |
| A24F 47/00 | (2006.01) |
| A61M 11/04 | (2006.01) |
| A61M 15/06 | (2006.01) |
| H02J 50/20 | (2016.01) |

(52) U.S. Cl.
CPC ......... *A24F 47/008* (2013.01); *A61M 11/042* (2014.02); *A61M 15/06* (2013.01); *H02J 50/20* (2016.02); *A61M 2205/3653* (2013.01); *A61M 2205/502* (2013.01); *A61M 2205/8206* (2013.01); *A61M 2205/8237* (2013.01)

(58) Field of Classification Search
None
See application file for complete search history.

(56) References Cited

U.S. PATENT DOCUMENTS

| | | |
|---|---|---|
| 1,771,366 A | 7/1930 | Wyss et al. |
| 2,057,353 A | 10/1936 | Whittemore, Jr. |
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |

(Continued)

FOREIGN PATENT DOCUMENTS

| | | |
|---|---|---|
| AU | 276250 | 7/1965 |
| CA | 2 641 869 | 5/2010 |

(Continued)

OTHER PUBLICATIONS

International Search Report dated Oct. 26, 2017 in International application No. PCT/IB2017/054021 filed Jul. 3, 2017.

*Primary Examiner* — Thor S Campbell
(74) *Attorney, Agent, or Firm* — Womble Bond Dickinson (US) LLP (57) ABSTRACT

A radio frequency (RF) to direct current (DC) converter for an aerosol delivery device is provided. The aerosol delivery device includes a power source, and an antenna configured to receive radio-frequency (RF) energy from an external RF transmitter. The aerosol delivery device also includes a power harvesting circuitry configured to receive radio-frequency RF energy from an external RF transmitter, and harvest power from the RF energy to power or charge at least one electronic component of the aerosol delivery device.

12 Claims, 6 Drawing Sheets

(56) References Cited

U.S. PATENT DOCUMENTS

| | | |
|---|---|---|
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 9,603,386 B2 * | 3/2017 | Xiang .................. A24F 47/008 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0058361 A1* | 3/2009 | John .................. A61N 1/3785 |
| | | 320/128 |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1* | 8/2010 | Robinson .............. A24F 47/008 |
| | | 131/194 |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0226236 A1* | 9/2011 | Buchberger .......... A61M 11/041 |
| | | 128/200.23 |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0133213 A1* | 5/2012 | Borke .................... H02J 17/00 |
| | | 307/104 |
| 2012/0160251 A1 | 6/2012 | Hammel et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0152956 A1* | 6/2013 | von Borstel .......... A24F 47/002 |
| | | 131/329 |
| 2013/0192619 A1 | 8/2013 | Tucker et al. |
| 2013/0220315 A1* | 8/2013 | Conley ................ A24F 47/008 |
| | | 128/202.21 |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1* | 4/2014 | Ampolini ............ A24F 47/008 |
| | | 131/328 |
| 2014/0109921 A1 | 4/2014 | Chen |
| 2014/0157583 A1 | 6/2014 | Ward et al. |
| 2014/0174459 A1* | 6/2014 | Burstyn ................ A24F 47/008 |
| | | 131/273 |

(56) References Cited

U.S. PATENT DOCUMENTS

| | | | |
|---|---|---|---|
| 2014/0184148 A1* | 7/2014 | Van Der Lee | H04B 5/0031 320/108 |
| 2014/0190496 A1* | 7/2014 | Wensley | A24F 47/008 131/273 |
| 2014/0209105 A1* | 7/2014 | Sears | F22B 1/28 131/328 |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2014/0278258 A1 | 9/2014 | Shafer | |
| 2014/0345631 A1 | 11/2014 | Bowen et al. | |
| 2015/0007838 A1 | 1/2015 | Fernando et al. | |
| 2015/0053217 A1 | 2/2015 | Steingraber et al. | |
| 2016/0037826 A1 | 2/2016 | Hearn et al. | |
| 2016/0120221 A1 | 5/2016 | Mironov et al. | |
| 2017/0180178 A1* | 6/2017 | Gollakota | H04K 3/25 |
| 2017/0290371 A1* | 10/2017 | Davis | A24F 47/008 |
| 2018/0248409 A1* | 8/2018 | Johnston | H02J 50/20 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | 2015192336 A1 | 12/2015 |
| WO | 2017/0103887 | 6/2017 |

* cited by examiner

RADIO FREQUENCY TO DIRECT CURRENT CONVERTER FOR AN AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference.

It would be desirable to provide aerosol delivery devices with functionality for converting radio frequency energy to direct current power.

BRIEF SUMMARY

The present disclosure relates to aerosol delivery devices, methods of forming such devices, and elements of such devices. The present disclosure thus includes, without limitation, the following example implementations. In some example implementations, an apparatus embodied as an aerosol delivery device or a cartridge for an aerosol delivery device is provided. The apparatus may comprise a housing defining a reservoir configured to retain aerosol precursor composition, and a heating element controllable to activate and vaporize components of the aerosol precursor composition. The apparatus may also comprise power harvesting circuitry configured to receive radio-frequency (RF) energy from an external RF transmitter, and harvest power from the RF energy to power or charge at least one electronic component such as one or more electronic components.

In some example implementations of the apparatus of the preceding or any subsequent example implementation, or any combination thereof, the power harvesting circuitry being configured to harvest power from the RF energy includes being configured to harvest power from the RF energy to power the at least one electronic component including a display or sensor, or the heating element.

In some example implementations of the apparatus of any preceding or any subsequent example implementation, or any combination thereof, the power harvesting circuitry being configured to harvest power from the RF energy includes being configured to harvest power from the RF energy to charge the at least one electronic component including a power source (e.g., a rechargeable lithium ion battery (LiB), rechargeable thin film solid state battery (SSB), rechargeable supercapacitor or the like) configured to power a display or sensor, or the heating element.

In some example implementations of the apparatus of any preceding or any subsequent example implementation, or any combination thereof, the power harvesting circuitry includes an antenna configured to receive the RF energy, and a converter configured to harvest the power from the RF energy so received.

In some example implementations of the apparatus of any preceding or any subsequent example implementation, or any combination thereof, the power harvesting circuitry includes an accumulator, and the power harvesting circuitry being configured to harvest power from the RF energy includes being configured to harvest power from the RF energy to charge the accumulator configured to power or charge the at least one electronic component.

In some example implementations of the apparatus of any preceding or any subsequent example implementation, or any combination thereof, the power harvesting circuitry further includes an inverting or non-inverting operational amplifier, and the accumulator being configured to power or charge the at least one electronic component includes being configured to discharge current through the inverting or non-inverting operational amplifier configured to amplify and regulate the current.

In some example implementations of the apparatus of any preceding or any subsequent example implementation, or any combination thereof, the power harvesting circuitry further includes a resistor, and the accumulator being configured to power the at least one electronic component includes being configured to discharge current through the resistor, the resistor having a variable resistance and thereby the current having at least a variable amperage that effects a variable wattage, and in at least one instance the resistor being or including a potentiometer.

In some example implementations of the apparatus of any preceding or any subsequent example implementation, or any combination thereof, the power harvesting circuitry includes a converter configured to harvest the power from the RF energy, and a photovoltaic cell configured to harvest power from light energy, the at least one electronic component being powered or charged from either the converter or photovoltaic cell, or switchably from both the converter and photovoltaic cell.

In some example implementations, a control body coupled or coupleable with a cartridge to form an aerosol delivery device is provided. The cartridge contains an aerosol precursor composition and is equipped with a heating element controllable to activate and vaporize components of the aerosol precursor composition. The control body may include a control component configured to control the heating element to activate and vaporize components of the aerosol precursor composition, and power harvesting circuitry configured to receive radio-frequency (RF) energy from an external RF transmitter, and harvest power from the RF energy to power or charge at least one electronic component.

In some example implementations of the control body of the preceding or any subsequent example implementation, or any combination thereof, the power harvesting circuitry being configured to harvest power from the RF energy includes being configured to harvest power from the RF energy to power the at least one electronic component including a display or sensor, or the heating element.

In some example implementations of the control body of any preceding or any subsequent example implementation, or any combination thereof, the power harvesting circuitry being configured to harvest power from the RF energy includes being configured to harvest power from the RF energy to charge the at least one electronic component including a power source configured to power a display or sensor, or the heating element.

In some example implementations of the control body of any preceding or any subsequent example implementation, or any combination thereof, the power harvesting circuitry includes an antenna configured to receive the RF energy, and a converter configured to harvest the power from the RF energy so received.

In some example implementations of the control body of any preceding or any subsequent example implementation, or any combination thereof, the power harvesting circuitry includes an accumulator, and the power harvesting circuitry being configured to harvest power from the RF energy includes being configured to harvest power from the RF energy to charge the accumulator configured to power or charge the at least one electronic component.

In some example implementations of the control body of any preceding or any subsequent example implementation, or any combination thereof, the power harvesting circuitry further includes an inverting or non-inverting operational amplifier, and the accumulator being configured to power or charge the at least one electronic component includes being configured to discharge current through the inverting or non-inverting operational amplifier configured to amplify and regulate the current.

In some example implementations of the control body of any preceding or any subsequent example implementation, or any combination thereof, the power harvesting circuitry further includes a resistor, and the accumulator being configured to power the at least one electronic component includes being configured to discharge current through the resistor, the resistor having a variable resistance and thereby the current having a variable amperage that effects a variable wattage, and in at least one instance the resistor being or including a potentiometer.

In some example implementations of the control body of any preceding or any subsequent example implementation, or any combination thereof, the power harvesting circuitry includes a converter configured to harvest the power from the RF energy, and a photovoltaic cell configured to harvest power from light energy, the at least one electronic component being powered or charged from either the converter or photovoltaic cell, or switchably from both the converter and photovoltaic cell.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or capacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

Figure 1:
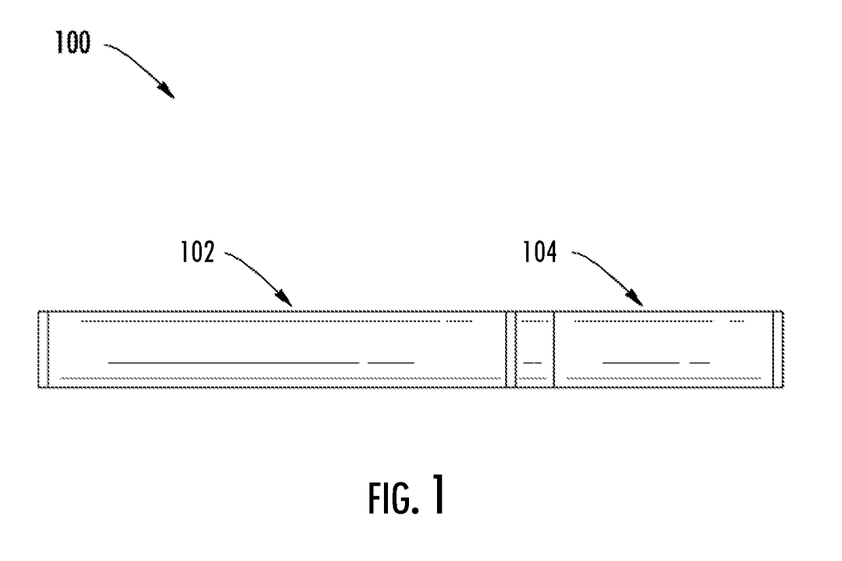
FIG. 1 illustrates a side view of an aerosol delivery device including a cartridge coupled to a control body, according to an example implementation of the present disclosure.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular or rhomboidal in cross-section, which may lend itself to greater compatibility with a substantially flat or thin-film power source, such as a power source including a flat battery. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical wall outlet, connection to a car charger (i.e., a cigarette lighter receptacle), connection to a computer, such as through a universal serial bus (USB) cable or connector, or connection to a photovoltaic cell (sometimes referred to as a solar cell) or solar panel of solar cells. Some examples of suitable recharging technology are described below. Further, in some example implementations, the cartridge may comprise a single-use cartridge, as disclosed in U.S. Pat. No. 8,910,639 to Chang et al., which is incorporated herein by reference in its entirety.

Figure 2:
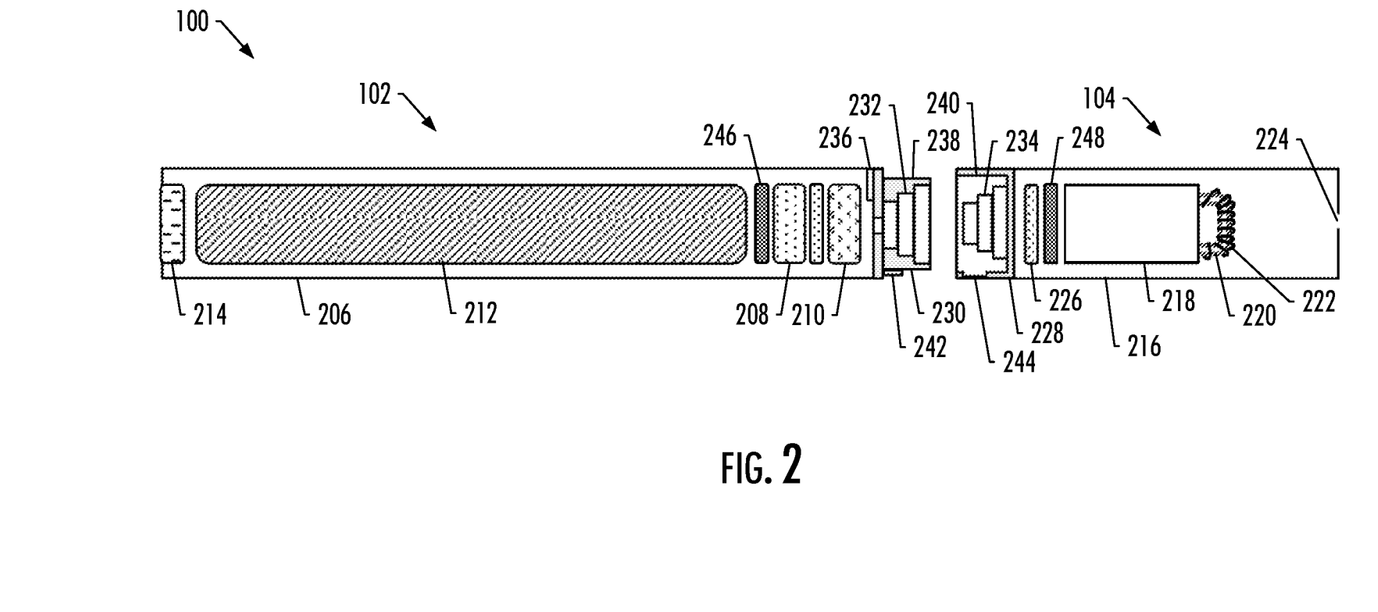
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include various electronic components such as a control component 208 (e.g., a microprocessor, individually or as part of a microcontroller), a flow sensor 210, a power source 212 and one or more light-emitting diodes (LEDs) 214, and such components can be variably aligned. In addition to the flow sensor 210, the various electronic components of the control body may also include a number of other suitable sensors such as an accelerometer, gyroscope, proximity sensor, or the like.

The power source 212 may be or include a suitable power supply such as a lithium-ion battery, solid-state battery or supercapacitor as disclosed in U.S. patent application Ser. No. 14/918,926 to Rajesh et al. which is incorporated herein by reference. Examples of suitable solid-state batteries include STMicroelectronics' EnFilm™ rechargeable solid-state lithium thin-film batteries. Examples of suitable supercapacitors include electric double-layer capacitor (EDLC), a hybrid capacitor such as a lithium-ion capacitor (LIC), or the like.

The LEDs 214 may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED.

In some implementations, the various electronic components of the control component 208 may include a display. The display may be configured to output various information including information regarding a status of the aerosol delivery device 100, information unrelated to the status of the aerosol delivery device (e.g., the present time), and/or non-informative graphics (e.g., graphics provided for user entertainment purposes). Thereby, the display may be configured to output any or all of the information described above (e.g., a remaining or used portion of the capacity of the power source 212) in any form such as graphical form and/or a numerical form. Further, in some implementations operation or the display may be controlled by the input mechanism or a separate input mechanism. The display, for example, may be a touchscreen and thus may be configured for user input. In some implementations, the display may provide icons, menus, or the like configured to allow a user to make control selections related to the functioning of the aerosol delivery device, check a specific status of the device, or the like. Although the display is illustrated as encompassing only a relatively small portion of the aerosol delivery device, it is understood that the display may cover a significantly greater portion of the aerosol delivery device.

The cartridge 104 can be formed of a cartridge shell 216 enclosing a reservoir 218 that is in fluid communication with a liquid transport element 220 adapted to wick or otherwise transport an aerosol precursor composition stored in the reservoir housing to a heater 222 (sometimes referred to as a heating element). In various configurations, this structure may be referred to as a tank; and accordingly, the terms "tank," "cartridge" and the like may be used interchangeably to refer to a shell or other housing enclosing a reservoir for aerosol precursor composition, and including a heater. In some example, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be a resistive heating element such as a wire coil, microheater or the like. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), Titanium (Ti), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend) to allow for egress of formed aerosol from the cartridge 104.

In addition to the heater 222, the cartridge 104 also may include one or more other electronic components 226. These electronic components may include an integrated circuit, a memory component, a sensor (e.g., an accelerometer, gyroscope, proximity sensor, or the like), or the like. In some examples, the electronic components of the cartridge may include a display similar to that described above with respect to the control body, and which may be in addition to or in lieu of the control body having a display. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection and under-voltage lock out. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off power to the heater when the aerosol delivery device is not be drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. The electronic components may include a microprocessor or processor core, and a memory. In some examples, the control component may include a microcontroller with integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

In some examples, the control body 102 may include a power harvesting circuitry 246 configured to radio-frequency (RF) energy for powering or charging one or more electronic components of either or both the control body 102 or cartridge 104. As described above, for example, the control body may include various electronic components such as a sensor (e.g., flow sensor 210), power source 212, heater 222, display or the like. The power harvesting circuitry may be configured to harvest power from the RF energy within a frequency range of 800 to 1000 megahertz (MHz).

Examples of suitable power harvesting circuitries are disclosed in U.S. Pat. App. Pub. Nos. 2005/0104553, filed Oct. 18, 2004, to Mickle et al.; and 2011/0101789, filed Dec. 1, 2009, to Salter, Jr. et al., each of which is incorporated herein by reference in its entirety. Further examples of suitable power harvesting circuitries are disclosed in Priya, Shashank, and Daniel J. Inman, eds. Energy harvesting technologies. Vol. 21: 280-321. New York: Springer, 2009. Other power harvesting circuits that may be employed include the power harvesting circuits that have been incorporated in the Powerharvester™ receiver products by Powercast™.

The power harvesting circuitry 246 may be configured to receive RF energy from an external RF transmitter, and harvest power from the RF energy to power or charge one or more electronic components. For example, power harvested from RF energy may be utilized for powering a sensor of the aerosol delivery device 100 which may be or include an accelerometer, gyroscope, proximity sensor, or the like. In another example, power harvested from RF energy may be utilized for powering a display (e.g., LED display) of the aerosol delivery device.

Figure 3:
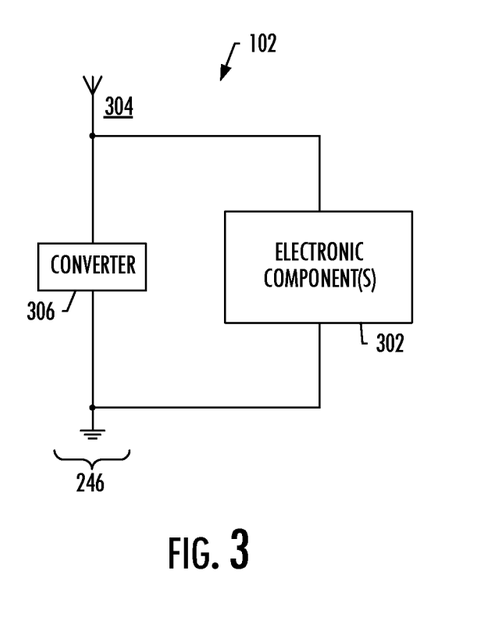
FIGS. 3, 4, 5 and 6 illustrate various elements of the control body, according to various example implementations.

FIG. 3 more particularly illustrates the control body 102 of FIGS. 1 and 2 including the power harvesting circuitry 246 for powering or charging at least one electronic component 302 according to example implementations of the present disclosure. It should be noted that the electronic component(s) may be included in either or both the control body or cartridge 104 of the aerosol delivery device 100. As shown in FIG. 3, the power harvesting circuitry 246 may include an antenna 304 configured to receive the RF energy from the external RF transmitter, and a converter 306 configured to harvest the power from the RF energy.

Figure 4:
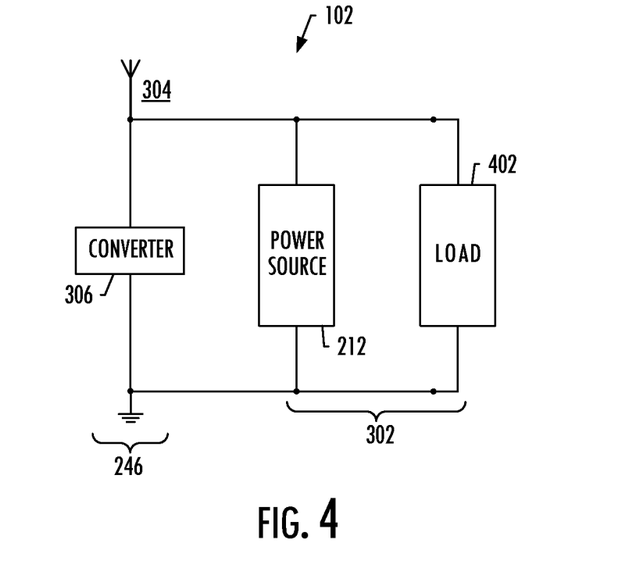
Figure 5:
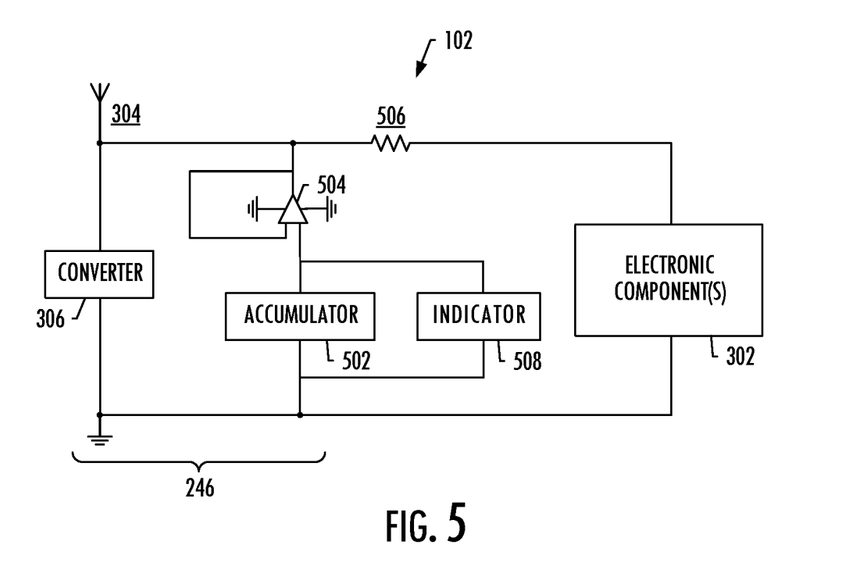
Figure 6:
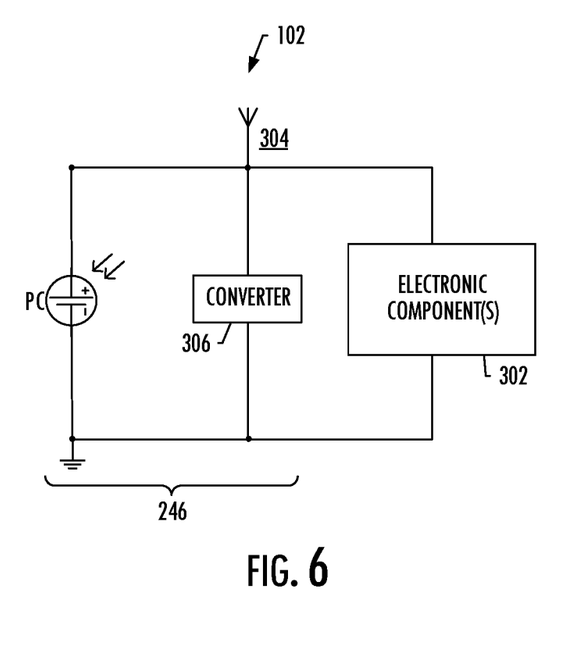

FIGS. 4, 5 and 6 more particularly illustrate the control body 102 of FIG. 3 according to example implementations of the present disclosure. In accordance with some example implementations, the power source 212 of the control body 102 may be a rechargeable power source such as a rechargeable lithium ion battery (LiB), thin film solid state battery (SSB), or thin film super capacitor, and thus may be combined with any type of recharging technology, some of which may include using power harvested from RF energy. Thus, as shown in FIG. 4, in some example implementations, the at least one electronic component may include the power source, and the power harvesting circuitry 246 may be configured to harvest power from the RF energy to charge the power source.

As also shown in FIG. 4, the power source 212 may be connected to an electrical load 402 that includes various components of the control body to form an electrical circuit, and that may also include the heater 222 when the control body is coupled with the cartridge 104. More particularly, the electrical load may include the control component 208, which may also be coupled with the power source. In some implementations, the at least one electronic component may include the electrical load. In some implementations, the power harvested from the RF energy may be utilized for powering the various electronic components independent of, or in conjunction with the power source 212 (e.g., a lithium-ion battery, solid-state battery or supercapacitor). Thus, in some of these examples, the power harvesting circuitry 246 may be configured to harvest power from the RF energy to charge the power source, and the power source may be configured to power at least one other electronic component such a display or sensor, or the heater.

As shown in FIG. 5, in some example implementations, the power harvesting circuitry 246 includes an accumulator 502. In these example implementations, the power harvesting circuitry may be configured to harvest power from the RF energy to charge the accumulator configured to power or charge the at least one electronic component 302. The accumulator may be or include a suitable energy storage component such as a rechargeable lithium-ion battery, rechargeable thin film solid-state battery, rechargeable supercapacitor or the like. In some examples, the converter 306 may be configured to convert RF energy to DC power and store the power in the accumulator until a charge threshold of the accumulator is achieved. In instances in which the charge threshold of the accumulator has been achieved, the accumulator may be configured to boost an output voltage level thereof, using a direct current (DC) voltage boost converter circuitry. The voltage output may be disabled upon the charge declining below the charge threshold.

As also shown in FIG. 5, in some examples, the power harvesting circuitry 246 may include a number of other electronic components, such as amplifiers, analog-to-digital (ADC) converters, digital-to-analog (DAC) converters, resistors, indicators and the like to form the electrical circuit. In some examples, the accumulator 502 may be configured to discharge power through an operational amplifier 504 (e.g., inverting or non-inverting operational amplifier) in which the operational amplifier may be configured to amplify and regulate a discharge current from the accumulator to the at least one electronic component 302. The power harvesting circuitry may also include a variable resistor 506 in which the accumulator may be configured to discharge current through the resistor to the at least one electronic component. The resistor may have a variable resistance and thereby the current may have variable amperage that effects a variable wattage. For example, the resistor may be or include a three-terminal resistor such as a potentiometer. As such the resistor may be configured to adjust a voltage or current range of the power being discharged from the accumulator to the at least one electronic component. In some examples, an output voltage of the accumulator may be set to 3.3 volts, and the voltage may be adjustable from 1.8 volts up to 5.25 volts using the variable resistor.

The power harvesting circuitry 246 may also include an indicator 508 (e.g., light-emitting diodes (LEDs) 214 that may include organic LEDs) configured to visually indicate a voltage level of the accumulator 502. In some examples, the indicator may be coupled to a control component 208 and included in the control body 102. In these examples, the power harvesting circuitry may generate and transmit a signal to the control component for driving the indicator in which the signal may correspond to a voltage level of the accumulator.

As shown in FIG. 6, in some examples, the power harvesting circuitry 246 may include a photovoltaic cell PC configured to harvest power from light energy. In these examples, the at least one electronic component 302 may be powered or charged from either the converter 306 or the photovoltaic cell, or switchably from both the converter and photovoltaic cell. In some example implementations, the at least one electronic component may be configured to receive power from the converter, and switch to the photovoltaic cell only after the converter has discharged by at least a threshold amount.

Referring again to FIG. 2, in addition to or in lieu of the control body 102, the cartridge 104 may include power harvesting circuitry 248 that may be configured and function similar to the power harvesting circuitry 246 of the control body as discussed above with reference to FIGS. 3-6. For example, the cartridge may include a power harvesting circuitry configured to harvest power from RF energy for powering or charging the various electronic components of the cartridge, and in some instances the control body, such as a heater 222, sensor, display or other suitable electronic components. In these examples, the power harvesting circuitry may be configured to receive RF energy from an external RF transmitter, and harvest power from the RF energy to power or charge various electronic components according to various example implementations discussed herein.

Figure 7:
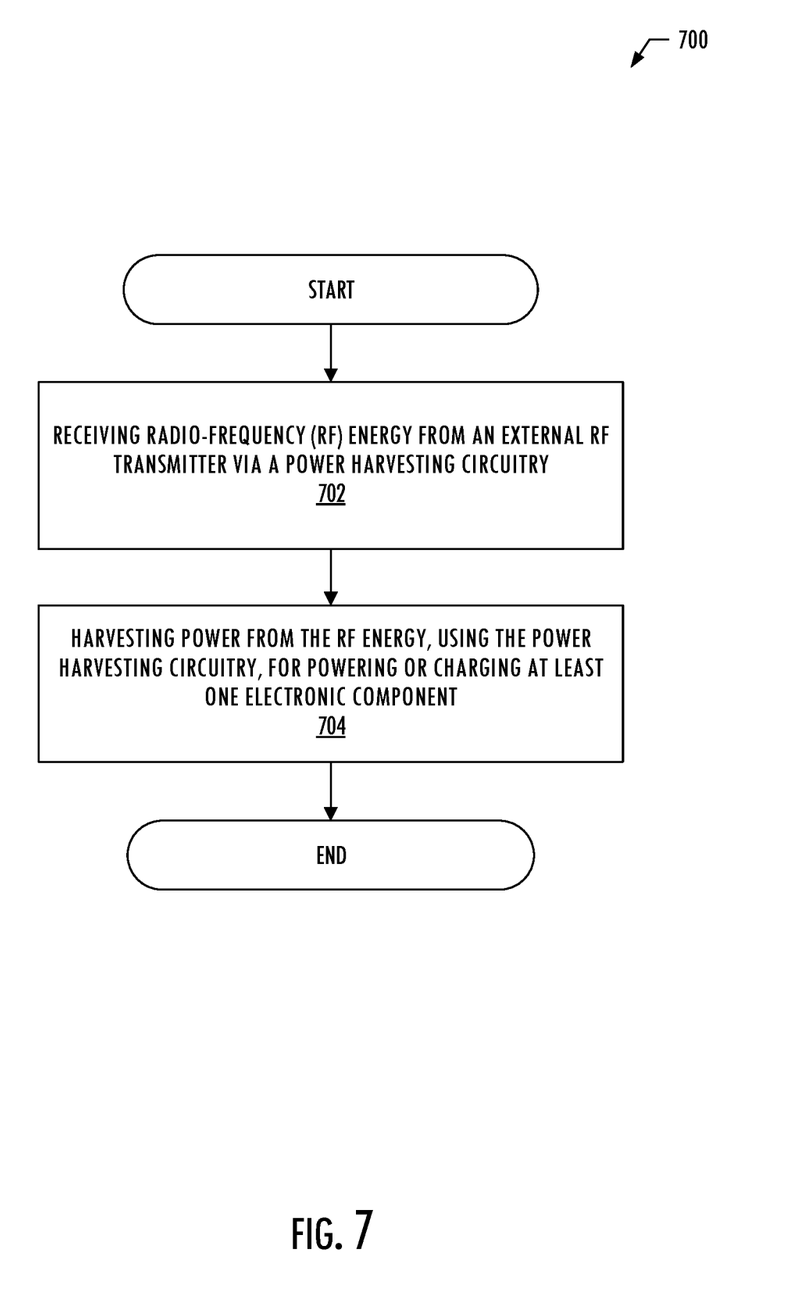
FIG. 7 illustrates various operations in a method for controlling an aerosol delivery device, according to an example implementation.

FIG. 7 illustrates various operations in a method 700 for controlling an aerosol delivery device according to example implementations of the present disclosure. The aerosol delivery device may include a control body coupled or coupleable with a cartridge to form the aerosol delivery device. The cartridge may be equipped with a heating element configured to activate and vaporize components of an aerosol precursor composition. The method may comprise receiving RF energy from an external RF transmitter via an antenna, as shown at block 702. The method may also comprise harvesting power from the RF energy, using a converter, for powering or charging a at least one electronic component, as shown at block 704.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-7 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus embodied as an aerosol delivery device or a cartridge for an aerosol delivery device, the apparatus comprising:
a housing defining a reservoir configured to retain aerosol precursor composition;
a heating element controllable to activate and vaporize components of the aerosol precursor composition; and
power harvesting circuitry including an accumulator and a resistor, the power harvesting circuitry being configured to receive radio-frequency (RF) energy from an external RF transmitter, and harvest power from the RF energy to charge the accumulator, the power harvesting circuitry being configured to power or charge at least one electronic component including the accumulator being configured to discharge current through the resistor, the resistor having a variable resistance and thereby the current having a variable amperage that effects a variable wattage, and in at least one instance the resistor being or including a potentiometer.

2. The apparatus of claim 1, wherein the power harvesting circuitry being configured to harvest power from the RF energy includes being configured to harvest power from the RF energy to power the at least one electronic component including a display or sensor, or the heating element.

3. The apparatus of claim 1, wherein the power harvesting circuitry being configured to harvest power from the RF energy includes being configured to harvest power from the RF energy to charge the at least one electronic component including a power source configured to power a display or sensor, or the heating element.

4. The apparatus of claim 1, wherein the power harvesting circuitry includes an antenna configured to receive the RF energy, and a converter configured to harvest the power from the RF energy so received.

5. The apparatus of claim 1, wherein the power harvesting circuitry further includes an inverting or non-inverting operational amplifier, and the accumulator being configured to power or charge the at least one electronic component includes being configured to discharge current through the inverting or non-inverting operational amplifier configured to amplify and regulate the current.

6. The apparatus of claim 1, wherein the power harvesting circuitry includes a converter configured to harvest the power from the RF energy, and a photovoltaic cell configured to harvest power from light energy, the at least one electronic component being powered or charged from either the converter or photovoltaic cell, or switchably from both the converter and photovoltaic cell.

7. A control body coupled or coupleable with a cartridge to form an aerosol delivery device, the cartridge containing an aerosol precursor composition and equipped with a heating element controllable to activate and vaporize components of the aerosol precursor composition, the control body comprising:
a control component configured to control the heating element to activate and vaporize components of the aerosol precursor composition; and
power harvesting circuitry including an accumulator and a resistor, the power harvesting circuitry being configured to receive radio-frequency (RF) energy from an external RF transmitter, and harvest power from the RF energy to charge the accumulator, the power harvesting circuitry being configured to power or charge at least one electronic component including the accumulator being configured to discharge current through the resistor, the resistor having a variable resistance and thereby the current having a variable amperage that effects a variable wattage, and in at least one instance the resistor being or including a potentiometer.

8. The control body of claim 7, wherein the power harvesting circuitry being configured to harvest power from the RF energy includes being configured to harvest power from the RF energy to power the at least one electronic component including a display or sensor, or the heating element.

9. The control body of claim 7, wherein the power harvesting circuitry being configured to harvest power from the RF energy includes being configured to harvest power from the RF energy to charge the at least one electronic component including a power source configured to power a display or sensor, or the heating element.

10. The control body of claim 7, wherein the power harvesting circuitry includes an antenna configured to receive the RF energy, and a converter configured to harvest the power from the RF energy so received.

11. The control body of claim 7, wherein the power harvesting circuitry further includes an inverting or non-inverting operational amplifier, and the accumulator being configured to power or charge the at least one electronic component includes being configured to discharge current through the inverting or non-inverting operational amplifier configured to amplify and regulate the current.

12. The control body of claim 7, wherein the power harvesting circuitry includes a converter configured to harvest the power from the RF energy, and a photovoltaic cell configured to harvest power from light energy, the at least one electronic component being powered or charged from either the converter or photovoltaic cell, or switchably from both the converter and photovoltaic cell.

* * * * *